United States Patent [19]
Shima

[11] Patent Number: 5,938,442
[45] Date of Patent: Aug. 17, 1999

[54] COUPLED ARTIFICIAL TOOTH ASSEMBLY

[75] Inventor: Fumio Shima, Komatsushima, Japan

[73] Assignee: Shiken Corporation, Tokushima, Japan

[21] Appl. No.: 09/107,325

[22] Filed: Jun. 30, 1998

[30] Foreign Application Priority Data

Apr. 22, 1998 [JP] Japan .................................. 10-112281

[51] Int. Cl.⁶ ................................................. A61C 13/00
[52] U.S. Cl. .......................... 433/167; 433/171; 433/191;
433/199.1; 433/213
[58] Field of Search ..................................... 433/196, 167,
433/191, 171, 213, 199.1

[56] References Cited

U.S. PATENT DOCUMENTS

| | | | |
|---|---|---|---|
| 1,518,075 | 12/1924 | Kesling | 433/196 |
| 4,583,947 | 4/1986 | Hazar | 433/213 |
| 4,681,543 | 7/1987 | Monroy | 433/196 |
| 4,780,082 | 10/1988 | Schwartz | 433/213 |

FOREIGN PATENT DOCUMENTS

| | | | |
|---|---|---|---|
| 519399 | 4/1955 | Belgium | 433/191 |
| 46515 | 3/1939 | Netherlands | 433/191 |

*Primary Examiner*—John J. Wilson
*Assistant Examiner*—Patrick A. Hilsmier
*Attorney, Agent, or Firm*—Wenderoth, Lind & Ponack, L.L.P.

[57] ABSTRACT

Coupled artificial teeth which minimize the shaping work of gum when manufacturing a denture model and eliminates residues in the plaster mold are disclosed. A coupled artificial tooth assembly includes a plurality of teeth coupled together only by wax. On the front side of the gum, the wax covers a base portion of each of the artificial teeth and fills the interdental papillae, while exposing the tooth crowns. On the backside of the gum, the wax fills the space around the bottom portion of each of the artificial teeth so that the bottom portion is almost completely exposed. The backside of the gum is substantially flush with the bottom portions of the artificial teeth and forms a bow-shaped curved surface similar in shape to a real human gum.

6 Claims, 2 Drawing Sheets

FIG. 1A  FIG. 1B  FIG. 1C
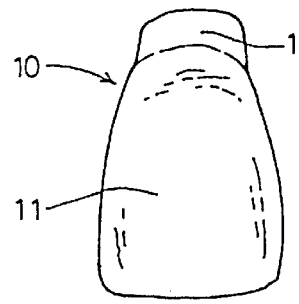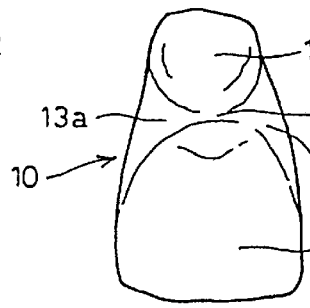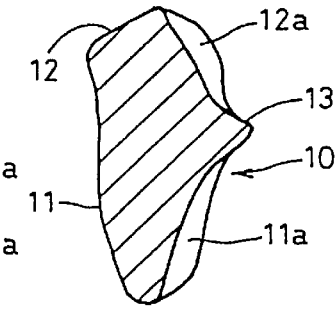
FIG. 2A
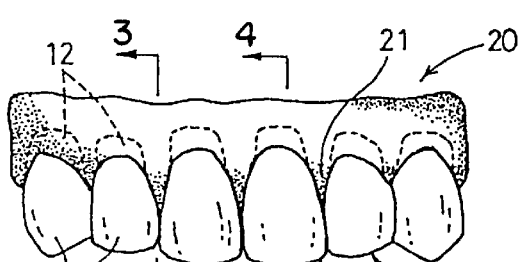
FIG. 2B
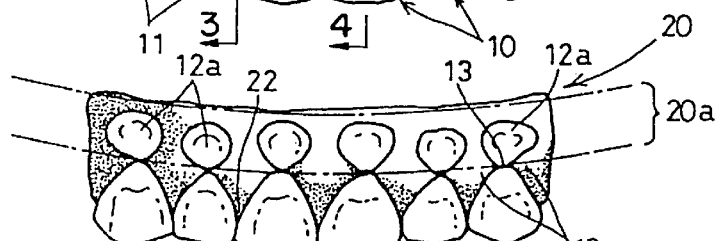
FIG. 2C
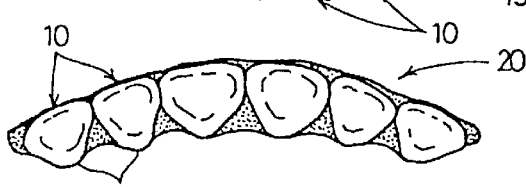
FIG. 2D
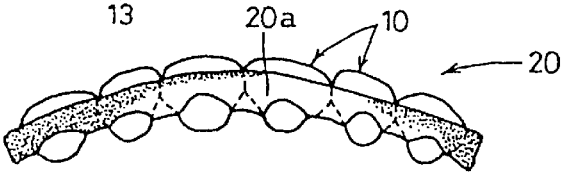

5,938,442

COUPLED ARTIFICIAL TOOTH ASSEMBLY

BACKGROUND OF THE INVENTION

This invention relates to a coupled artificial tooth assembly manufactured by coupling together artificial teeth into a segment and used in the manufacturer of dentures.

Dentures are manufactured by forming a wax bank in a toothless jaw model and fixing artificial teeth one by one to the wax bank while the wax bank is softened with e.g. a burner.

The wax bank is then carved with a chisel into a shape similar to actual gum to manufacture wax dentures. This requires much trouble and skilled hands.

In unexamined Japanese patent publication 6-261917, a plurality of artificial teeth coupled together by wax and thread are disclosed. With this arrangement, there is no need to arrange artificial teeth one by one in a toothless jaw model.

But even if such coupled artificial teeth are used, the gum has to be carved or shaped with a chisel. The bottoms of teeth have a complicated shape, and the gum is disposed between the teeth in a complicated manner. Thus, it is extremely troublesome to shape the gum into proper shape.

Further, in the prior art publication, a core material such as thread is used in addition to wax to couple artificial teeth together. Thus, when the wax is removed from the denture model which is embedded in plastic and manufactured in the above manner, the core material such as thread will remain in the plaster and be difficult to remove.

An object of the present invention is to minimize the gum shaping work when manufacturing a denture model and to eliminate any residues in a plaster mold.

SUMMARY OF THE INVENTION

According to this invention, there is provided a coupled artificial tooth assembly which includes a plurality of teeth coupled together only by wax. This wax forms a gum. On the front side of the gum, the wax covers a base portion of each of the artificial teeth and fills papillae between the adjacent artificial teeth. On the back of the gum, the wax fills the space around a bottom of the base portion of each of the artificial teeth so that the bottom is almost completely exposed, and so that the backside of the gum is substantially flush with the bottom of the base portion of the artificial teeth. This forms a bow-shaped curved surface similar in shape to a human gum.

Other features and objects of the present invention will become apparent from the following description made with reference to the accompanying drawings, in which:

BRIEF DESCRIPTION OF THE DRAWINGS

FIGS. 1A, 1B and 1C are a front view, a back view and a vertical sectional view of an artificial tooth;

FIGS. 2A, 2B, 2C and 2D are a front view, a back artificial teeth according to this invention, respectively;

DETAILED DESCRIPTION OF THE PREFERRED EMBODIMENT

Figure 3:
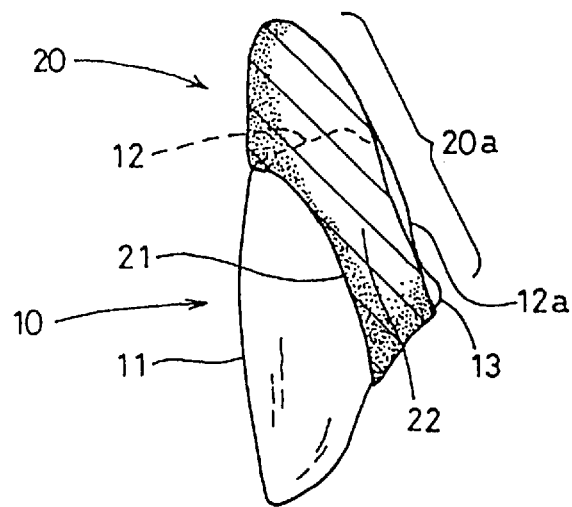
FIG. 3 is a sectional view taken along line 3—3 of FIG. 2A.

Embodiments of this invention are described with reference to the drawings. FIGS. 1A–1C show an example of an artificial tooth in the form of incisors. As shown, the artificial tooth 10 includes a crown 11 exposed from a gum and a base 12 to be fixed to the gum. The crown 11 and the base 12 have in their backsides a shallow recess 11a and a bottom 12a, respectively. (It is to be understood that bottom 12a is used to identify a particular portion of tooth 10 and is not intended to designate a directional orientation.) A rib 13 is defined between the recess 11a and the bottom 12a. The artificial teeth represent six upper and lower foreteeth and are similar in shape, though some may be bigger than others.

FIGS. 2A–2D show coupled artificial teeth coupled together by wax. As shown, on front side, the wax forming a gum 20 substantially fills the tooth bases 12 and wedge-shaped papillae 21 between and adjacent teeth. While on the back side, the wax fills substantially diamond-shaped portions 22 defined by the edges of the bottoms 12a and inclined surfaces 13a on both sides of the crowns 11. With this arrangement, the bottoms 12a are mostly exposed as shown in FIG. 2B. A thin film of wax is inevitably formed because a small amount of wax flow into the recess of each bottom 12a.

Figure 4:
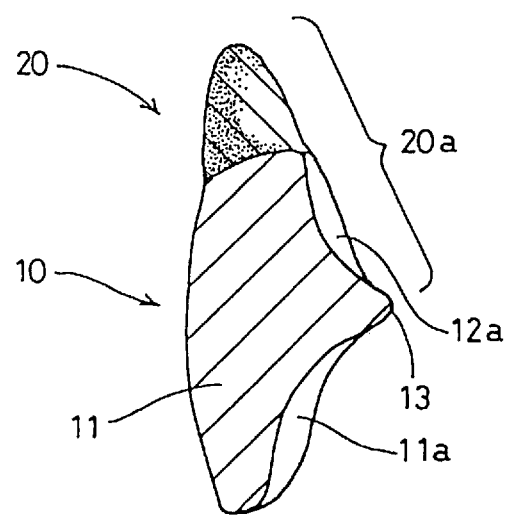
FIG. 4 is a sectional view taken along line 4—4 of FIG. 2A.

FIGS. 3 and 4 are vertical sections of the gum 20. As shown in FIG. 3, between the adjacent artificial teeth 10, the sides of the bases 12 are completely filled with wax. Thus, the artificial teeth 10 are rigidly held in position by the wax. Also, the back side of the gum is substantially flush with the bottoms 12a, so that it is very similar in shape to a real human gum.

As shown in FIG. 4, wax is present only near the tip of the bottom 12a of each artificial tooth 10, and practically no wax is present at the bottoms 12a, as with a real gum. That is, the back side of the gum 20 forms, as a whole, a bow-shaped or oval curved surface 20a extending continuously in the longitudinal direction of the artificial teeth while being kept substantially flush with the bottoms 12a.

Figure 5:
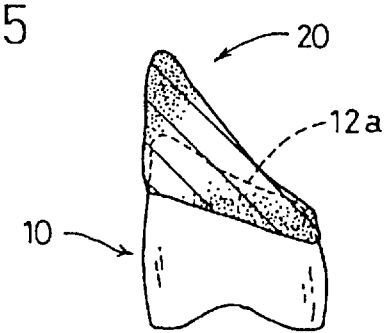
FIG. 5 is a sectional view of a second embodiment of the present invention and shows, in particular, a molar coupling structure.

In a second embodiment of the invention, which covers the case of molars, as shown in FIG. 5, there may appear a slight difference in parallelism between the backs of the bottoms 12a and the back of the gum 20 or the two may not be completely flush. But the teeth 10 are held by the gum 20 in substantially the same manner as above.

The coupled artificial teeth may be any combination of incisors, canines, premolars and molars. But it is customary to prepare artificial teeth in the form of tooth sets on the upper and lower jaws with each having six foreteeth, three each on either side, and four molars on either side.

To use such coupled artificial teeth, a wax bank is formed on a toothless jaw model, and the artificial teeth are bonded thereto while the wax is softened or melted. Any unnecessary portions of the teeth are then removed by cutting the wax gum 20 of the teeth with e.g. a knife. Since the gum 20 has no core material such as thread, it can be cut easily and accurately. Since the gum 20 is very similar in shape to a real gum, after the artificial teeth have been bonded to the wax bank, any additional shaping with a chisel is practically unnecessary except removing burrs at joint portions.

The coupled artificial teeth assembly of this invention can be used not only for full dentures but also for partial dentures. The wax forming the gum 20 may be synthetic wax, natural wax or a mixture thereof as long as it can retain shape at normal temperature. The material for the artificial teeth 10 is also not limited.

According to this invention, artificial teeth are coupled together only by wax, and the gum portion is very similar in shape to a real gum. This makes it possible to manufacture wax dentures very easily without the need for skilled hands.

When the wax is removed by melting from the wax denture which is solidified in a plaster mold, no core such as thread will remain in the plaster mold. Thus, the wax is easily removed.

What is claimed is:

1. An artificial tooth assembly comprising:

a gum having a front side and a back side and comprising a plurality of papillae; and a plurality of teeth, each tooth comprising a crown and a base portion which has a front, a back, and a bottom surface, each tooth being positioned in said gum between said papillae such that said front side of said gum covers said front of said base portion of each tooth and said back side of said gum covers said back of said base portion of each tooth leaving said bottom surface exposed so that said back side of said gum is substantially flush with said bottom surface of each tooth.

2. The artificial tooth assembly of claim 1, wherein: said gum is bow-shaped and made of wax.

3. The artificial tooth assembly of claim 1, wherein: said back of each tooth comprises a recess portion and a rib, said rib being defined at one end by said bottom surface of said base portion and at an opposite end by said recess portion.

4. The artificial tooth assembly of claim 3, wherein: said back side of said gum covers said rib.

5. The artificial tooth assembly of claim 1, wherein: said back side of said gum forms a substantially diamond-shaped portion between each tooth, said substantially diamond-shaped portion covering said rib of each tooth.

6. The artificial tooth assembly of claim 1, wherein: said crown of each tooth is exposed.

* * * * *